United States Patent [19]

Nagel

[11] 4,153,686

[45] May 8, 1979

[54] PROCESS FOR THE PREPARATION OF GLUCOPROTEINS AS WELL AS THE USE THEREOF

[76] Inventor: Hans-Hugo Nagel, Haynstrasse 19, 2000 Hamburg 20, Fed. Rep. of Germany

[21] Appl. No.: 760,423

[22] Filed: Jan. 18, 1977

[30] Foreign Application Priority Data

Jan. 28, 1976 [DE] Fed. Rep. of Germany ....... 2603122

[51] Int. Cl.$^2$ .............................................. A61K 37/02
[52] U.S. Cl. ................................ 424/176; 260/112 R; 260/117; 260/121; 424/177
[58] Field of Search ................... 260/112 R, 117, 121; 424/177, 176

[56] References Cited

U.S. PATENT DOCUMENTS

| 3,637,640 | 1/1972 | Huber | 424/177 X |
| 3,847,890 | 11/1974 | Green et al. | 424/177 X |

*Primary Examiner*—Walter C. Danison
*Attorney, Agent, or Firm*—Cushman, Darby & Cushman

[57] ABSTRACT

The use of a stabilized glucoprotein for the preparation of medicaments with a potentiating action of active substances is described wherein the separate glucoprotein is stabilized with an inorganic electrolyte and/or a saccharide and albumin mixture combinations with antibiotics, ampicillin, etc., are described.

7 Claims, No Drawings

PROCESS FOR THE PREPARATION OF GLUCOPROTEINS AS WELL AS THE USE THEREOF

The invention relates to a process for the preparation of glucoproteins from proteins and carbohydrates, as well as to the use of the glucoproteins prepared according to the invention.

It is known that glucoproteins are widely naturally occurring biologically important substances comprising protein and sugars covalently bonded to functional groups of amino acids, which must not be nucleic acids. Glucoproteins exercise important biological functions as transfer proteins, inhibitors and complement factors. For example, in medicine there is frequently a glucoprotein participation in the case of acute or chronic rheumatic illnesses and skin diseases.

The ratio of protein to polysaccharide in the glucoproteins can vary within wide limits. Glucoproteins in which the carbohydrate forms a relatively large proportion of the total molecule (more than about 10%) are generally called mucoproteins.

A particularly simple process for the preparation of synthetic glucoproteins has been found whereby if they are suitably stabilised they can be stored for a virtually unlimited period. It has surprisingly been found that the thus obtained glucoproteins exert a very considerable potentiating action on a wide range of medicaments, and in many cases also extend the action spectrum.

The subject matter of the invention is a process for the preparation of stabilised glucoproteins, characterised in that an aqueous suspension of yeast is reacted with monosaccharides and native albumin as starting substances, the resulting glucoproteins are separated from the reaction medium and the separated glucoproteins are stabilised by adding inorganic electrolytes and/or saccharide/albumin mixtures.

It is admittedly known that amino acids and corresponding albumin molecules react with aldehyde and acetals accompanied by the formation of insoluble large molecules. However, it was surprising that under the influence of yeast ferments monosaccharides can be directly reacted with albumin to give soluble glucoproteins.

In the process according to the invention, it is advantageously possible to use an aqueous suspension of yeast, e.g. saccharomyces cerevisiae or torula utilis. The reaction is advantageously performed in the neutral range, that is to say at pH values of approximately 6 to 7.5 and at ambient temperature, that is to say approximately 18 to 22° C.

As starting substances lactalbumin and gelatin have proved suitable as albumin components and lactose and glucose as monosaccharide components.

It has been experimentally established that for the performance of the process according to the invention, yeast ferments are necessary as catalysts. However, no detailed investigation has been performed to establish which yeast ferments catalyse glucoprotein formation from native albumin and monosaccharides.

The working up of the reaction product for separating the glucoproteins obtained can take place by methods known per se from albumin chemistry. The glucoprotein is preferably separated from the impurities by dialysis and is subsequently dried under optimum gentle conditions, for example by centrifuging, solvent extraction or preferably lyophilization (freeze-drying). The glucoproteins obtained are water-soluble and can be redissolved from water. Their average molecular weight can vary within wide limits and in particularly preferred manner is in the range 55,000 to 65,000.

The pure glucoproteins prepared according to the invention are not stable, making stabilisation necessary prior to their further use. It has been found that both inorganic electrolytes and sacchride/albumin mixtures are suitable for stabilisation purposes. The first group in particular includes salts of metals of the first, second and eighth groups of the periodic system, for example chlorides, carbonates and phosphates of potassium, sodium, magnesium, calcium and iron. The second group preferably includes mixtures of lactalbumin, lactose and D-glucose, although it is also possible to use other albumin substances and other aldehyde sugars. According to a particularly preferred embodiment of the invention, stabilisation is performed by adding the inorganic salts and an albumin/sugar suspension to the aqueous glucoprotein solution, followed by drying under gentle conditions in the manner described hereinbefore. The albumin/sugar mixture is used in a large weight excess based on the glucoprotein, preferably in a ratio of $10^3$ to $10^6:1$, and more particularly at approximately $10^5:1$. The thus obtained glucoprotein is stable and suitable for further use. A further object of the invention is the use of the preferably stabilised glucoproteins prepared according to the invention for potentiating medicaments. It has been found in a completely surprising manner that the novel glucoproteins increase the action of therapeutics, hormones and chemotherapeutics and in part widen their action spectrum. Although no complete explanation can be given for this observation, it can be assumed that transfer improvement effects are involved because glucoproteins are constituents of the cell membranes. For example, the increased action in the case of antibiotics could be based on an increased inhibition of specific transfer peptidases necessary in bacteria cell wall synthesis.

The potentiating action is observed even with very low glucoprotein concentrations so that they are preferably used in a ratio of 1 part by weight glucoprotein to $10^2$ to $10^6$ parts by weight, and preferably approximately $10^4$ parts by weight of active medicament substance. According to the present observations, the action is optimum if the average molecular weight of the glucoproteins is in the range of approximately 55,000 to 65,000.

As is further illustrated by the following Examples, the minimum inhibiting concentration (MIC) values of the glucoprotein/ampicillin combinations according to the invention are, for example, much lower than those of ampicillin alone. In addition, resistance formation does not occur and suprisingly the action spectrum extends not only to all gram-positive and gram-negative stimulants, but also to fungi and viruses which are resistant to ampicillin alone. Similar surprising potentiating actions also occur with other antibiotics.

Glucoprotein/dexamethasone combinations have the same action as ten times the dose of dexamethasone alone. A similar increased action was observed in combinations of glucoprotein/Norfenefrin and glucoprotein/phenylbutazone as compared with the active substances alone.

The following Examples illustrate the invention in a non-limitative manner.

EXAMPLE 1

10 g of lactalbumin, 2 g of lactose and 1 g of yeast were suspended in 250 ml of water and dialysed for 24 hours in a dialyzer at 20° C. relative to distilled water. After only 8 hours the passage of albumin was detected with the aid of the ninhydrin-reaction. After 24 hours dialysis dialysate was carefully concentrated in vacuo and the solid residue was redissolved from a little water, whereupon the crystals were dried in a desiccator. A glucoprotein with an average molecular weight of 60,000 was obtained.

For stabilisation purposes in each case 1 mg of glucoprotein was added to a suspension of 65 g of albumin/sugar (50% lactalbumin, 25% lactose, 25% D-glucose) which also contained traces of sodium and potassium chloride, calcium and iron carbonate and magnesium phosphate. After thorough mixing the suspension was carefully concentrated at ambient temperature under reduced pressure, whereupon the concentrate was dehydrated by freeze-drying. Glucoprotein is present in stabilised form in the thus obtained powder so that its potentiating action remains unchanged.

In a control test 10 g of lactalbumin and 2 g of lactose were dialysed in 250 ml of water for 24 hours in a dialyser at 20° C. relative to distilled water and in the absence of yeast. At the end of this time no albumin could be detected in the distilled water, whilst the quantity of sugar was distributed in approximately uniform manner. Thus, no reaction takes place in the absence of yeast.

EXAMPLE 2

Example 1 was repeated, whereby over a period of three hours and accompanied by stirring at 20° C., 10 g of gelatin was swelled in 200 ml of distilled water and then mixed with 3 g of glucose and 2 g of yeast. After 24 hours the mixture was dialysed relative to distilled water at ambient temperature. After only 1 hour the passage of albumin through the dialysis membrane could be detected by means of the lead acetate precipitation reaction. The dialysate was again concentrated in vacuo at 20° C., whereupon the crude product obtained was redissolved. The glucoprotein obtained had an average molecular weight of approximately 55,000.

The glucoprotein was subsequently stabilised in the manner described in Example 1.

EXAMPLE 3

The stabilised glucoprotein prepared according to Example 1 was combined in the following manner with D-(2-amino-2-phenylacetamido)-3,3-dimethyl-7-oxo-4-thia-1-azabicyclo-[3,2,0]-heptane-2-carboxylic acid (ampicillin) by dry mixing 13.75 parts of ampicillin-sodium and 86.25 parts by weight of the albumin/sugar mixture, the latter containing 0.001375 parts by weight of glucoprotein (glucoprotein: ampicillin ratio=$1:10^4$).

In the following comparative tests the combination product according to the invention is compared with commercial ampicillin-sodium.

A. Determination of the bactericidal activity in vitro

The bactericidal action was tested in the cylinder test with nutrient medium in the form of agar foil (PA) and inoculated agar foil (PCA) following an 18-hour incubation at 37° C. The test agar was prepared by filling Petri dishes having a diameter of 10 cm with 14 ml of basic agar (PA). When the medium became solid it was coated with 4 ml of inoculated agar (PCA). Prior to being placed in the Petri dishes the inoculated agar was mixed at 40° C. with 0.1 ml of a non-diluted preliminary culture of test bacteria which had been cultured for 18 hours at 37° C.

Following a period of action of 20 minutes, 6 steel cylinders (external diameter 8 mm, internal diameter 6 mm, length 10 mm) were pressed into the solidified agar masses. In each case three of the cylindrical depressions were filled with the comparative substance and the test substance in distilled water. Dilutions which became necessary were carried out with pH 7 phosphate buffer. The diffusion was carried out for 18 hours at 37° C. The diffusion range was subsequently determined and the sensitivity was calculated compared with the standard samples. The values obtained are summarised in the following Table. In each case they are average values of three individual measurements.

Table 1

| Bacterial strain | | | Bactericidal action (MIC in $\gamma$ active substance/ml) | |
|---|---|---|---|---|
| | | | Test substance | |
| | | | Ampicillin | Ampicillin/ Glucoprotein |
| stapyloc. aur. | ATCC | 11522 | 0.06 | 0.001 |
| staphyloc. aur. | NCTC | 6571 | 0.06 | 0.001 |
| stapyloc. aur. | ATCC | 6538 P | | |
| (Penicillinase forming substance) | | | resistant | 0.001 |
| strept. pyogenes | ATCC | 8668 | 0.03 | 0.0005 |
| strept. faecalis | ATCC | 8043 | 2.0 | 0.015 |
| strept. faecalis | ATCC | 10541 | 1.0 | 0.015 |
| strept. faecalis | ATCC | 19433 | 2.0 | 0.015 |
| strept. pneumon. | ATCC | 6301 | 0.06 | 0.0005 |
| strept. pneumon. | ATCC | 6302 | 0.06 | 0.0005 |
| h. influencae | ATCC | 19418 | 0.25 | 0.004 |
| ps. aeruginosa | NCTC | 10662 | 240 | 0.04 |
| escherichia coli | NCTC | 10418 | 8 | 0.013 |

The numerical values clearly show that the ampicillin potentiated with the glucoprotein prepared according to the invention has a bactericidal activity which is improved by at least two powers of ten compared with ampicillin alone. Glucoprotein alone has no bactericidal activity.

The following Table 2 shows the MIC-values relative to different bacterial strains. Not only are the lower MIC values for the combination according to the invention noteworthy, but in addition the action relative to those strains which form Penicillinase and against which ampicillin alone is completely ineffective is especially surprising.

Table 2

Bactericidal MIC-values in γ/ml

| No. | Type of Strain | No. of Strains | Test Substance | 2000 | 250 | 100 | 50 | 25 | 12.5 | 6.2 | 4.7 | 3.1 | 2.4 | 1.8 | 1.2 | 0.8 | 0.6 | 0.4 | 0.3 | 0.2 | 0.1 | 0.05 | 0.02 | 0.01 | 0.005 | 0.002 | 0.001 | 0.0005 | 0.0002 |
|---|---|---|---|---|---|---|---|---|---|---|---|---|---|---|---|---|---|---|---|---|---|---|---|---|---|---|---|---|
| 1 | proteus mirabilis a | 50 | A | | 3 | 1 | 3 | 1 | 2 | 1 | 1 | 18 | 2 | 18 | | | | | | | | | | | | | | | |
| 2 | not a Penicillinase forming-substance | | A + G | | | | | | | | | | | | 1 | | | | | 2 | 2 | 2 | 2 | 40 | | | | | |
| 3 | proteus mirabilis b | | A | 50 | | | | | | | | | | | | | | | | | | | | | | | | | |
| 4 | Penicillinase-forming substance | 50 | A + G | | | | | | | | | | | 1 | 1 | | | | | | 1 | 2 | 2 | 2 | 40 | | | | |
| 5 | escherichia | | A | | 3 | 1 | 8 | 3 | 1 | 14 | 8 | 7 | 1 | 2 | | | | 1 | | | | | | | | | | | |
| 6 | coli | 50 | A + G | | | | | | | | | | | 4 | 6 | 12 | 28 | | | | 1 | 11 | 17 | 19 | | | | | |
| 7 | staphyl. aur. a | 50 | A | | | | | | | | | | | | | | | | | 1 | 1 | | | | | | | | |
| 8 | not a Penicillinase-forming substance | | A + G | | | | | | | | | | | | | | | | | | | 1 | 2 | 43 | 1 | 1 | 1 | | |
| 9 | staphyl. aur. b | 50 | A | 50 | | | | | | | | | | | | | | | | | | | | | | | | | |
| 10 | Penicillinase-forming substance | | A + G | | | | | | | | | | | | | | | | | 1 | | | | | | | | | |
| 11 | strept. | 50 | A + G | | | | | | | 2 | | | 2 | 3 | 8 | 12 | 24 | | | 1 | 1 | 1 | 1 | 2 | 4 | 18 | 24 | | |
| 12 | pyogenes | 50 | A | | | | | | | | | | | | | | | | | 1 | 1 | | 1 | 2 | | 10 | 36 | | |
| 13 | aerobacter | 50 | A + G | | | | | | | | | | | 1 | 1 | 1 | 2 | 5 | 8 | 8 | | | | | | | | | |
| 14 | aeroges | | A | 50 | | | | | | | | | | | | | | | 8 | 8 | | 7 | 9 | | | | | | |
| 15 | psuedomonas | 50 | A + G | 50 | | | | | | | | | | | | | | | | 8 | | | | | | | | | |
| 16 | aeruginosa | 50 | A | | | | | | | 2 | 2 | 4 | 2 | 5 | 9 | 10 | 11 | 13 | | | | | | | | | | | |
| 17 | salmonella | | A + G | | | | | 2 | | 2 | 4 | 4 | 5 | 7 | 22 | | | | | | | | | | | | | | |
| 18 | enteritid | 50 | A + G | | | | | | | | | | | | | | | | | 3 | 2 | 2 | 3 | 15 | | 25 | | | |

A = Ampicillin-sodium
A + G = Ampicillin-sodium + Glucoprotein (ratio 10⁴:1)

B. Fungicidal activity

The MIC-values for the fungicidal activity of the combination product were determined according to the provisions of the American Soc. of Clinical Microbiology, Manual of Clinical Microbiology, 2nd Edition (Washington, D.C.). The MIC-values given in Table 3 are therefore particularly surprising because ampicillin alone has no fungicidal activity which can be evaluated in practice.

Table 3

| Test Strain | MIC in γ/ml |
|---|---|
| Aspergillus fumigatum | 0.05–0.1 |
| flavus | |
| Blastomyces dermatitidis | 0.1–0.3 |
| Candida albicans | |
| guillermondii | |
| psuedotropicalis | 0.05–0.1 |
| stellatoides | |
| Coccidioides immitis | 0.05–0.1 |
| Cryptococcus neoformans | 0.05–0.1 |
| Epidermophyton floccosum | 0.1–0.3 |
| Geotricum candidum | 0.1–0.3 |
| Histoplasma capsulatum | 0.05–0.1 |
| duboisii | |
| Microsporum audouinii | |
| fulvum | |
| gypseum | 0.05–0.1 |
| persicolor | |
| Nocardia asteroides | 0.1–0.4 |
| Rhodotorula glutinis | 0.1–0.4 |
| rubra | |
| Sporotrichum schenkii | 0.05–0.1 |
| Torulopsis glabata | |
| pintolopesii | 0.05–0.3 |
| Trichophyton tonsurans | 0.1–0.4 |
| Trichomonas vaginalis | 0.1–0.3 |
| Trichosporum cutaneum | 0.05–0.3 |

C. Virus activity

The ampicillin/glucoprotein combination product according to the invention was clinically tested relative to the following virus infections:
- 10 Cases of Influenza A virus
- 10 Cases of Influenza B virus
- 5 Cases of Parainfluenza virus, type 1 (HA 2)
- 5 Cases of Parainfluenza virus, type 2 (Greer)
- 5 Cases of Parainfluenza virus, Type 3 (HA 1)
- 10 Cases of Respiratori syncytical virus (Long)
- 10 Cases of Adenovirus The research was carried out by means of the complement fixation test (Micromethod according to J. L. Sever, J. Immunol. 88, 320–329 (1962)). The sera were considered as antibody-positive if a four times positive reaction was found in the case of a dilution of at least 1:4.

Treatment took place with tablets which in each case contained 55 mg of ampicillin-trihydrate and 5.5 γ of glucoprotein in stabilised form. On the first and second day two tablets were administered four times daily and on the third to seventh day one tablet four times daily. 40 of the treated cases were completely free from symptoms after four days and the remaining cases after fifteen days.

EXAMPLE 4

The potentiating action of the glucoprotein prepared according to the invention was tested on dexamethasone. The test substances used were dexamethasone alone and dexamethasone combined with glucoprotein (weight ratio $10^4:1$).

In clinical tests 10 patients suffering from primary chronic polyarthritis were tested within the scope of a comparative test, whereby for the determination of the activity of the treatment the BSG and ASLO titres were used.

The results obtained are given in the following Table 4. It was surprisingly found that by means of the combination product according to the invention roughly the same action was obtained as when using a ten times higher dose of dexamethasone alone.

Table 4

| | | | Pre-treatment | | | after 5 days treatment with 0.5 mg Dexam 3 × daily perorally | | | after 14 days without treatment (Plazebos) | | | after 5 days treatment 3 × daily 0.05 mg Dexam + Glycoprotein($10^4$:1) perorally | | |
|---|---|---|---|---|---|---|---|---|---|---|---|---|---|---|
| | | | BSG after | | | BSG after | | | BSG after | | | BSG after | | |
| Patient | Sex | Age | 1 h. | 2 h. | ASLO i.E. | 1h. | 2 h. | ASLO i.E. | 1h. | 2 h. | ASLO i.E. | 1 h. | 2 h. | ASLO i.E. |
| 1. | M | 35 | 65 | 90 | 800 | 25 | 30 | 200 | 70 | 100 | 900 | 20 | 35 | 100 |
| 2. | M | 38 | 60 | 80 | 900 | 20 | 35 | 100 | 60 | 90 | 900 | 20 | 30 | 200 |
| 3. | M | 39 | 70 | 90 | 800 | 20 | 40 | 200 | 70 | 90 | 800 | 22 | 38 | 200 |
| 4. | M | 36 | 52 | 82 | 1000 | 25 | 45 | 300 | 60 | 88 | 900 | 24 | 41 | 200 |
| 5. | M | 40 | 65 | 85 | 800 | 30 | 50 | 200 | 72 | 98 | 1000 | 31 | 43 | 300 |
| 6. | F | 37 | 60 | 90 | 1000 | 25 | 42 | 300 | 58 | 92 | 1000 | 24 | 40 | 200 |
| 7. | F | 38 | 50 | 100 | 900 | 20 | 38 | 200 | 54 | 102 | 800 | 21 | 36 | 200 |
| 8. | F | 40 | 50 | 85 | 800 | 24 | 36 | 300 | 48 | 92 | 900 | 26 | 39 | 100 |
| 9. | F | 39 | 45 | 90 | 1000 | 22 | 34 | 200 | 51 | 101 | 1000 | 24 | 35 | 100 |
| 10. | F | 38 | 50 | 100 | 900 | 24 | 38 | 200 | 49 | 98 | 900 | 25 | 41 | 100 |
| Average | | | 56.7 | 89.2 | 890 | 23.5 | 38.8 | 220 | 59.2 | 95.1 | 910 | 23.7 | 37.8 | 170 |

EXAMPLE 5

The potentiating action of glucoprotein prepared according to the invention was tested on phenyl-butazone. The same patients were treated as in Example 4. The test results given in Table 5 show an unexpected increase in action as a result of glucoprotein making it possible to reduce the dose to 1/10.

Table 5

| | | | Pre-treatment BSG after | | after 8 days treatment with 1.0 g phenylbutazone 3 × daily orally BSG after | | after 14 days without treatment (Plazebos) BSG after | | after 8 days treatment 3 × daily 0.1 g phenylbutazone + glucoprotein ($10^4$:1) perorally BSG after | |
|---|---|---|---|---|---|---|---|---|---|---|
| Patient | Sex | Age | 1 h. | 2 h. | 1 h. | 2 h. | 1 h. | 2 h. | 1 h. | 2 h. |
| 1. | M | 35 | 72 | 92 | 38 | 62 | 70 | 90 | 34 | 54 |

Table 5-continued

| | | | Pre-treatment BSG after | | after 8 days treatment with 1.0 g phenylbutazone 3 × daily orally BSG after | | after 14 days without treatment (Plazebos) BSG after | | after 8 days treatment 3 × daily 0.1 g phenylbutazone + glucoprotein (10⁴ :1) perorally BSG after | |
|---|---|---|---|---|---|---|---|---|---|---|
| Patient | Sex | Age | 1 h. | 2 h. | 1 h. | 2 h. | 1 h. | 2 h. | 1 h. | 2 h. |
| 2. | M | 38 | 59 | 81 | 40 | 60 | 60 | 84 | 30 | 50 |
| 3. | M | 39 | 68 | 88 | 38 | 50 | 65 | 92 | 36 | 48 |
| 4. | M | 36 | 55 | 90 | 35 | 60 | 58 | 92 | 32 | 50 |
| 5. | M | 40 | 62 | 95 | 38 | 45 | 60 | 98 | 34 | 45 |
| 6. | F | 37 | 61 | 92 | 30 | 62 | 64 | 100 | 28 | 52 |
| 7. | F | 38 | 56 | 101 | 28 | 58 | 58 | 102 | 30 | 52 |
| 8. | F | 40 | 54 | 92 | 32 | 62 | 58 | 98 | 30 | 48 |
| 9. | F | 39 | 48 | 92 | 28 | 60 | 50 | 100 | 26 | 52 |
| 10. | F | 38 | 50 | 98 | 25 | 60 | 54 | 102 | 28 | 54 |
| Average | | | 58.5 | 92.1 | 33.2 | 57.9 | 59.7 | 95.8 | 30.8 | 50.5 |

EXAMPLE 6

The potentiating action of glucoprotein prepared according to the invention was clinically investigated on Norfenefrin and 10 patients suffering from hypotonia were treated. The action of the test substances was determined by determining the systolic and diastolic blood pressure at mid-day in each case. There was no treatment on the first to seventh days, on the eighth to fourteenth days 3.0 mg of Norfenefrin were administered once daily, from the fifteenth to the twenty-first days treatment was again interrupted (administration of plazebos) and from the twenty-second to twenty-eighth days 0.3 mg of Norfenefrin combined with glucoprotein (weight ratio 10⁴:1) were administered once daily. In each case medication took place at 9:00 a.m., i.e. three hours before determining the blood pressure.

The test results given in Table 6 show that the combined product has much the same blood pressure increasing action as Norfenefrin at a ten times lower dose.

Table 6

| | | | Stystolic/diastolic blood pressure on | | | |
|---|---|---|---|---|---|---|
| Patient | Sex | Age | 7th day | 14th day | 21st day | 28th day |
| 1. | M | 19 | 90/60 | 120/70 | 80/50 | 134/80 |
| 2. | M | 18 | 90/60 | 125/75 | 80/55 | 130/80 |
| 3. | M | 19 | 90/60 | 125/80 | 80/50 | 130/80 |
| 4. | M | 19 | 85/50 | 125/80 | 80/50 | 135/80 |
| 5. | M | 19 | 80/40 | 125/80 | 80/45 | 135/80 |
| 6. | F | 18 | 85/45 | 130/80 | 90/50 | 135/80 |
| 7. | F | 18 | 90/50 | 130/80 | 85/45 | 135/80 |

Table 6-continued

| | | | Stystolic/diastolic blood pressure on | | | |
|---|---|---|---|---|---|---|
| Patient | Sex | Age | 7th day | 14th day | 21st day | 28th day |
| 8. | F | 19 | 90/55 | 130/70 | 80/50 | 140/80 |
| 9. | F | 19 | 85/50 | 130/80 | 90/50 | 135/80 |
| 10. | F | 19 | 85/50 | 120/70 | 85/50 | 135/80 |
| Average | | | 87.0/52.0 | 126.0/76.5 | 83.0/49.5 | 134.4/80.0 |

I claim:

1. Use of stabilized glucoprotein for the preparation of medicaments with a potentiating action on the active substances, whereby $10^2$ to $10^6$ parts by weight of the active medicament substance is used per 1 part by weight of glucoprotein, wherein said stabilized glucoprotein is prepared by reacting an aqueous suspension of yeast with monosaccharides and native albumin as starting substance, and separating the glucoprotein from the resulting reaction medium, and thereafter adding an inorganic electrolyte and/or a saccharide and albumin mixture thereto to stabilize the same.

2. Use according to claim 1, characterised in that the glucoprotein has an average molecular weight of 55,000 to 65,000.

3. Use according to claim 1, wherein lactose or glucose is used as the monosaccharide.

4. Use according to claim 1, wherein lactalbumin or gelatin is used as the albumin.

5. Use according to claim 1, wherein said reacting is performed at ambient temperature.

6. Use according to claim 1, wherein said reacting is performed at pH values of approximately 6 to 7.5.

7. Use according to claim 1, wherein said glucoprotein is separated by dialysis and dried.

* * * * *